United States Patent
Müller et al.

(10) Patent No.: US 6,768,004 B2
(45) Date of Patent: Jul. 27, 2004

(54) NUCLEOTIDE SEQUENCES ENCODING VARIABLE REGIONS OF HEAVY AND LIGHT CHAINS OF MONOCLONAL ANTIBODY 1F7, AN ANTI-IDIOTYPIC ANTIBODY REACTIVE WITH ANTI-HIV ANTIBODIES

(76) Inventors: Sybille Müller, 5235 Athens-Boonesboro Rd., Lexington, KY (US) 40509; Heinz Köhler, 5235 Athens-Boonesboro Rd., Lexington, KY (US) 40509

( * ) Notice: Subject to any disclaimer, the term of this patent is extended or adjusted under 35 U.S.C. 154(b) by 445 days.

(21) Appl. No.: 09/759,112

(22) Filed: Jan. 11, 2001

(65) Prior Publication Data

US 2003/0100741 A1 May 29, 2003

(51) Int. Cl.[7] .................. C07H 21/04; C07H 21/00; C12P 21/00; C12N 15/00; C12N 15/13
(52) U.S. Cl. .................. 536/23.53; 536/23.1; 536/53.5; 514/2; 514/44; 530/387.1; 530/387.2; 424/130.1; 424/131.1; 435/69.1; 435/320.1
(58) Field of Search ............... 424/130.1, 131.1, 424/133.1, 147.1, 148.1, 136.1, 141.1, 160.1; 435/5, 6, 7.1, 7.9, 69.1, 69.7, 327, 328, 339, 339.1, 344.1, 320.1, 325, 326, 354, 328.1; 436/518, 536, 548; 530/387.1, 387.2, 387.3, 388.15, 388.3, 388.35, 350, 388.1; 536/23.1, 23.4, 23.53

(56) References Cited

U.S. PATENT DOCUMENTS

| | | | |
|---|---|---|---|
| 4,843,011 A | | 6/1989 | Sarngadharan et al. |
| 5,217,895 A | | 6/1993 | Ohno |
| 5,849,583 A | | 12/1998 | Muller et al. |
| 5,928,904 A | * | 7/1999 | Holmes et al. ............ 435/69.6 |
| 6,057,421 A | | 5/2000 | Muller et al. |
| 6,506,383 B1 | * | 1/2003 | Black et al. ............. 424/154.1 |

OTHER PUBLICATIONS

Rudikoff et al. Proceedings of the National Acadamy of Sciences, USA, vol. 79, pp. 1979–1983, (Mar. 1982).*
Holmes et al., The Journal of Immunology, vol. 167, pp. 296–301 (Jul. 2001).*
Haruyama et al., Biological & Pharmaceutical Bulletin, vol. 25, No. 12, pp. 1537–1545 (Dec. 2002).*
Kasai et al., Journal of Immunological Methods, vol. 155, No. 1, pp. 77–89 (Oct. 1992).*
Matsushita et al., Journal of Virology, vol. 62, No 6, pp. 2107–2114 (Jun. 1988).*
Lohman et al., Gene, vol. 105, pp. 283–284 (1991).*
Zhou et al., Virology, vol. 174, pp. 9–17 (1990).*
S. Muller, et al. "Generation and specificity of monoclonal anti–idiotypic antibodies against human HIV–specific antibodies," J. Immunol. (1991) v147: 933–941.
H. Wang, et al., "Human monoclonal and polyclonal anti–human immunodeficiency virus–1 antibodies share a common clonotypic specificity," Eur. J. Immunol. (1992) v22: 1749–1755.
B. Herndier, et al. "A Non–lymphoma idiotype is indicative and predictive for B cell malignancies in AIDS," Hybridoma (1993) v12: 529–537.
S. Muller et al. "Stimulation of HIV–1–neutralizing antibodies in simian HIV–IIIB–infected macaques," Proc. Natl. Acad. Sci. USA (1998) v95:276–281.
S. Muller, et al., "An HIV–1 infection–related idiotype/clonotype (1F7) is expressed on antibodies directed to envelope glycoprotein in simian immunodeficiency virus– and chimeric simian/human immunodeficiency virus–infected rhesus monkeys," Hybridoma (1997) v16: 17–21.
Q. Wang, et al., "Identification of an idiotypic peptide recognized by autoantibodies in human immunodeficiency virus–1–infected individuals," J. Clin. Invest. (1995) v96: 775–780.
S. Chamat et al., "Two major groups of neutralizing anti–gp 120 antibodies exist in HIV–infected individuals," J. Immunol. (1992) v149:649–654.
H. Kohler et al., "Deceptive imprinting in the immune response against HIV–1" (1994) v15: 475–478.

* cited by examiner

Primary Examiner—James Housel
Assistant Examiner—Zachariah Lucas
(74) Attorney, Agent, or Firm—James H. Meadows Medicus Associates

(57) ABSTRACT

Nucleotide sequences encoding the variable heavy and light chains of the murine monoclonal antibody 1F7 are disclosed. The 1F7 antibody is an effective immune modulator that has anti-idiotypic binding affinity for anti-HIV antibodies. Polypeptides containing at least one complementarity-determining region (CDR) or framework-determining region (FR) of the variable heavy or variable light chains of 1F7, as well as the polynucleotides encoding them, can be used to modulate the immune response to HIV infection. Unnecessary, and potentially adverse, murine segments of the variable chains falling outside the CDRs can be replaced with human sequences to afford humanized chimeric antibodies and antibody fragments.

9 Claims, No Drawings

SEQUENCE LISTING

<160> NUMBER OF SEQ ID NOS: 38

<210> SEQ ID NO 1
<211> LENGTH: 37
<212> TYPE: DNA
<213> ORGANISM: mouse
<220> FEATURE:
<221> NAME/KEY: primer_bind
<222> LOCATION: (1)..(37)
<223> OTHER INFORMATION: 1F7 heavy chain 5' primer

<400> SEQUENCE: 1
actagtcgac atgaaatgca gctgggtcat sttcttc                                37

<210> SEQ ID NO 2
<211> LENGTH: 32
<212> TYPE: DNA
<213> ORGANISM: mouse
<220> FEATURE:
<221> NAME/KEY: primer_bind
<222> LOCATION: (1)..(32)
<223> OTHER INFORMATION: 1F7 heavy chain 3' primer

<400> SEQUENCE: 2
cccaagctta cgagggggaa gacatttggg aa                                     32

<210> SEQ ID NO 3
<211> LENGTH: 33
<212> TYPE: DNA
<213> ORGANISM: mouse
<220> FEATURE:
<221> NAME/KEY: primer_bind
<222> LOCATION: (1)..(33)
<223> OTHER INFORMATION: 1F7 light chain 5' primer

<400> SEQUENCE: 3
gggaattcat ggagacagac acactcctgc tat                                    33

<210> SEQ ID NO 4
<211> LENGTH: 30
<212> TYPE: DNA
<213> ORGANISM: mouse
<220> FEATURE:
<221> NAME/KEY: primer_bind
<222> LOCATION: (1)..(30)
<223> OTHER INFORMATION: 1F7 light chain 3' primer

<400> SEQUENCE: 4
cccaagctta ctggatggtg ggaagatgga                                        30

<210> SEQ ID NO 5
<211> LENGTH: 363
<212> TYPE: DNA
<213> ORGANISM: mouse
<220> FEATURE:
<221> NAME/KEY: gene
<222> LOCATION: (1)..(362)
<223> OTHER INFORMATION: 1F7 VH chain gene

<400> SEQUENCE: 5
caggttactc tgaaagagtc tggccctggg atattgcagc cctcccagac cctcagtctg        60
acttgttctt tctctgggtt ttcactgagc acttctggta tgggtgtgag ctggattcga       120
cagccttcag gaaagggtct ggagtggctg gcacacattt actgggatga tgacaagcgc       180
tataaaccat ccctgaagag ccggcttaca atctccaagg atacctccag caaccaggta       240

```
ttcctcaaga tcaccagtgt ggacactcga gatactgcca catactactg tgctcgaagg      300
gtctctctaa ctgcctatgc tatggactac tggggtcaag gaacctcagt caccgtctcc      360
tca                                                                    363
```

<210> SEQ ID NO 6
<211> LENGTH: 363
<212> TYPE: DNA
<213> ORGANISM: mouse
<220> FEATURE:
<221> NAME/KEY: CDS
<222> LOCATION: (1)..(363)
<223> OTHER INFORMATION: 1F7 VH chain gene

<400> SEQUENCE: 6

```
cag gtt act ctg aaa gag tct ggc cct ggg ata ttg cag ccc tcc cag        48
Gln Val Thr Leu Lys Glu Ser Gly Pro Gly Ile Leu Gln Pro Ser Gln
1               5                   10                  15 acc ctc agt ctg act tgt tct ttc tct ggg ttt tca ctg agc act tct        96
Thr Leu Ser Leu Thr Cys Ser Phe Ser Gly Phe Ser Leu Ser Thr Ser
            20                  25                  30 ggt atg ggt gtg agc tgg att cga cag cct tca gga aag ggt ctg gag       144
Gly Met Gly Val Ser Trp Ile Arg Gln Pro Ser Gly Lys Gly Leu Glu
        35                  40                  45 tgg ctg gca cac att tac tgg gat gat gac aag cgc tat aac cca tcc       192
Trp Leu Ala His Ile Tyr Trp Asp Asp Asp Lys Arg Tyr Asn Pro Ser
    50                  55                  60 ctg aag agc cgg ctt aca atc tcc aag gat acc tcc agc aac cag gta       240
Leu Lys Ser Arg Leu Thr Ile Ser Lys Asp Thr Ser Ser Asn Gln Val
65                  70                  75                  80 ttc ctc aag atc acc agt gtg gac act cga gat act gcc aca tac tac       288
Phe Leu Lys Ile Thr Ser Val Asp Thr Arg Asp Thr Ala Thr Tyr Tyr
                85                  90                  95 tgt gct cga agg gtc tct cta act gcc tat gct atg gac tac tgg ggt       336
Cys Ala Arg Arg Val Ser Leu Thr Ala Tyr Ala Met Asp Tyr Trp Gly
            100                 105                 110 caa gga acc tca gtc acc gtc tcc tca                                   363
Gln Gly Thr Ser Val Thr Val Ser Ser
        115                 120
```

<210> SEQ ID NO 7
<211> LENGTH: 121
<212> TYPE: PRT
<213> ORGANISM: mouse

<400> SEQUENCE: 7

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Arg Asp Thr Ala Thr Tyr Tyr
                85                  90                  95

Cys Ala Arg Arg Val Ser Leu Thr Ala Tyr Ala Met Asp Tyr Trp Gly
            100                 105                 110
```

-continued

```
Gln Gly Thr Ser Val Thr Val Ser Ser
        115                 120

<210> SEQ ID NO 8
<211> LENGTH: 90
<212> TYPE: DNA
<213> ORGANISM: mouse
<220> FEATURE:
<221> NAME/KEY: CDS
<222> LOCATION: (1)..(90)
<223> OTHER INFORMATION: 1F7 VH FR1 sequence

<400> SEQUENCE: 8 cag gtt act ctg aaa gag tct ggc cct ggg ata ttg cag ccc tcc cag    48
Gln Val Thr Leu Lys Glu Ser Gly Pro Gly Ile Leu Gln Pro Ser Gln
1               5                   10                  15 acc ctc agt ctg act tgt tct ttc tct ggg ttt tca ctg agc              90
Thr Leu Ser Leu Thr Cys Ser Phe Ser Gly Phe Ser Leu Ser
            20                  25                  30

<210> SEQ ID NO 9
<211> LENGTH: 30
<212> TYPE: PRT
<213> ORGANISM: mouse

<400> SEQUENCE: 9

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30

<210> SEQ ID NO 10
<211> LENGTH: 21
<212> TYPE: DNA
<213> ORGANISM: mouse
<220> FEATURE:
<221> NAME/KEY: CDS
<222> LOCATION: (1)..(21)
<223> OTHER INFORMATION: 1F7 VH CDR1 sequence

<400> SEQUENCE: 10 act tct ggt atg ggt gtg agc                                         21
Thr Ser Gly Met Gly Val Ser
1               5

<210> SEQ ID NO 11
<211> LENGTH: 7
<212> TYPE: PRT
<213> ORGANISM: mouse

<400> SEQUENCE: 11

Thr Ser Gly Met Gly Val Ser
1               5

<210> SEQ ID NO 12
<211> LENGTH: 42
<212> TYPE: DNA
<213> ORGANISM: mouse
<220> FEATURE:
<221> NAME/KEY: CDS
<222> LOCATION: (1)..(42)
<223> OTHER INFORMATION: 1F7 VH FR2 sequence

<400> SEQUENCE: 12 tgg att cga cag cct tca gga aag ggt ctg gag tgg ctg gca              42
Trp Ile Arg Gln Pro Ser Gly Lys Gly Leu Glu Trp Leu Ala
```

<210> SEQ ID NO 13
<211> LENGTH: 14
<212> TYPE: PRT
<213> ORGANISM: mouse

<400> SEQUENCE: 13

Trp Ile Arg Gln Pro Ser Gly Lys Gly Leu Glu Trp Leu Ala
1               5                   10

<210> SEQ ID NO 14
<211> LENGTH: 48
<212> TYPE: DNA
<213> ORGANISM: mouse
<220> FEATURE:
<221> NAME/KEY: CDS
<222> LOCATION: (1)..(48)
<223> OTHER INFORMATION: 1F7 VH CDR2 sequence

<400> SEQUENCE: 14 cac att tac tgg gat gat gac aag cgc tat aac cca tcc ctg aag agc      48
His Ile Tyr Trp Asp Asp Asp Lys Arg Tyr Asn Pro Ser Leu Lys Ser
1               5                   10                  15

<210> SEQ ID NO 15
<211> LENGTH: 16
<212> TYPE: PRT
<213> ORGANISM: mouse

<400> SEQUENCE: 15

His Ile Tyr Trp Asp Asp Asp Lys Arg Tyr Asn Pro Ser Leu Lys Ser
1               5                   10                  15

<210> SEQ ID NO 16
<211> LENGTH: 96
<212> TYPE: DNA
<213> ORGANISM: mouse
<220> FEATURE:
<221> NAME/KEY: CDS
<222> LOCATION: (1)..(96)
<223> OTHER INFORMATION: 1F7 VH FR3 sequence

<400> SEQUENCE: 16 cgg ctt aca atc tcc aag gat acc tcc agc aac cag gta ttc ctc aag      48
Arg Leu Thr Ile Ser Lys Asp Thr Ser Ser Asn Gln Val Phe Leu Lys
1               5                   10                  15 atc acc agt gtg gac act cga gat act gcc aca tac tac tgt gct cga      96
Ile Thr Ser Val Asp Thr Arg Asp Thr Ala Thr Tyr Tyr Cys Ala Arg
                20                  25                  30

<210> SEQ ID NO 17
<211> LENGTH: 32
<212> TYPE: PRT
<213> ORGANISM: mouse

<400> SEQUENCE: 17

Arg Leu Thr Ile Ser Lys Asp Thr Ser Ser Asn Gln Val Phe Leu Lys
1               5                   10                  15

Ile Thr Ser Val Asp Thr Arg Asp Thr Ala Thr Tyr Tyr Cys Ala Arg
                20                  25                  30

<210> SEQ ID NO 18
<211> LENGTH: 33
<212> TYPE: DNA
<213> ORGANISM: mouse

-continued

```
<220> FEATURE:
<221> NAME/KEY: CDS
<222> LOCATION: (1)..(33)
<223> OTHER INFORMATION: 1F7 VH CDR3 sequence

<400> SEQUENCE: 18 agg gtc tct cta act gcc tat gct atg gac tac                      33
Arg Val Ser Leu Thr Ala Tyr Ala Met Asp Tyr
1               5                   10

<210> SEQ ID NO 19
<211> LENGTH: 11
<212> TYPE: PRT
<213> ORGANISM: mouse

<400> SEQUENCE: 19

Arg Val Ser Leu Thr Ala Tyr Ala Met Asp Tyr
1               5                   10

<210> SEQ ID NO 20
<211> LENGTH: 33
<212> TYPE: DNA
<213> ORGANISM: mouse
<220> FEATURE:
<221> NAME/KEY: CDS
<222> LOCATION: (1)..(33)
<223> OTHER INFORMATION: 1F7 VH FR4 sequence

<400> SEQUENCE: 20 tgg ggt caa gga acc tca gtc acc gtc tcc tca                      33
Trp Gly Gln Gly Thr Ser Val Thr Val Ser Ser
1               5                   10

<210> SEQ ID NO 21
<211> LENGTH: 11
<212> TYPE: PRT
<213> ORGANISM: mouse

<400> SEQUENCE: 21

Trp Gly Gln Gly Thr Ser Val Thr Val Ser Ser
1               5                   10

<210> SEQ ID NO 22
<211> LENGTH: 330
<212> TYPE: DNA
<213> ORGANISM: mouse
<220> FEATURE:
<221> NAME/KEY: gene
<222> LOCATION: (1)..(330)
<223> OTHER INFORMATION: 1F7 VL chain gene

<400> SEQUENCE: 22
gacattgtgc tcaccaattc tccagcttct ttggctgtgt ctctagggca gagggccacc     60
atctcctgca aggccagcca aagtgttgat tatgatggtg atagttatat gtggtaccaa    120
cagaaaccag acagccacc caaactcctc acctatgctg catccaatct agaatctggg     180
atcccagcca ggtttagtgg cagtgggtct gggacagact tcaccctcaa catccatcct    240
gtggaggagg aggatgctgc aacctattac tgtcagcttt gtaatgagga tcctcccacg    300
ttcggtgctg ggaccaagct ggagctgaaa                                     330

<210> SEQ ID NO 23
<211> LENGTH: 330
<212> TYPE: DNA
<213> ORGANISM: mouse
<220> FEATURE:
```

<221> NAME/KEY: CDS
<222> LOCATION: (1)..(330)
<223> OTHER INFORMATION: 1F7 VL chain gene

<400> SEQUENCE: 23

```
gac att gtg ctc acc aat tct cca gct tct ttg gct gtg tct cta ggg       48
Asp Ile Val Leu Thr Asn Ser Pro Ala Ser Leu Ala Val Ser Leu Gly
1               5                   10                  15 cag agg gcc acc atc tcc tgc aag gcc agc caa agt gtt gat tat gat       96
Gln Arg Ala Thr Ile Ser Cys Lys Ala Ser Gln Ser Val Asp Tyr Asp
                20                  25                  30 ggt gat agt tat atg tgg tac caa cag aaa cca gga cag cca ccc aaa      144
Gly Asp Ser Tyr Met Trp Tyr Gln Gln Lys Pro Gly Gln Pro Pro Lys
            35                  40                  45 ctc ctc acc tat gct gca tcc aat cta gaa tct ggg atc cca gcc agg      192
Leu Leu Thr Tyr Ala Ala Ser Asn Leu Glu Ser Gly Ile Pro Ala Arg
        50                  55                  60 ttt agt ggc agt ggg tct ggg aca gac ttc acc ctc aac atc cat cct      240
Phe Ser Gly Ser Gly Ser Gly Thr Asp Phe Thr Leu Asn Ile His Pro
65                  70                  75                  80 gtg gag gag gag gat gct gca acc tat tac tgt cag ctt tgt aat gag      288
Val Glu Glu Glu Asp Ala Ala Thr Tyr Tyr Cys Gln Leu Cys Asn Glu
                85                  90                  95 gat cct ccc acg ttc ggt gct ggg acc aag ctg gag ctg aaa              330
Asp Pro Pro Thr Phe Gly Ala Gly Thr Lys Leu Glu Leu Lys
                100                 105                 110
```

<210> SEQ ID NO 24
<211> LENGTH: 110
<212> TYPE: PRT
<213> ORGANISM: mouse

<400> SEQUENCE: 24

```
Asp Ile Val Leu Thr Asn Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Trp Tyr Gln Gln Lys Pro Gly Gln Pro Pro Lys
            35                  40                  45

Leu Leu Thr Tyr Ala Ala Ser Asn Leu Glu Ser Gly Ile Pro Ala Arg
        50                  55                  60

Phe Ser Gly Ser Gly Ser Gly Thr Asp Phe Thr Leu Asn Ile His Pro
65                  70                  75                  80

Val Glu Glu Glu Asp Ala Ala Thr Tyr Tyr Cys Gln Leu Cys Asn Glu
                85                  90                  95

Asp Pro Pro Thr Phe Gly Ala Gly Thr Lys Leu Glu Leu Lys
                100                 105                 110
```

<210> SEQ ID NO 25
<211> LENGTH: 69
<212> TYPE: DNA
<213> ORGANISM: mouse
<220> FEATURE:
<221> NAME/KEY: CDS
<222> LOCATION: (1)..(69)
<223> OTHER INFORMATION: 1F7 VL FR1 sequence

<400> SEQUENCE: 25

```
gac att gtg ctc acc aat tct cca gct tct ttg gct gtg tct cta ggg       48
Asp Ile Val Leu Thr Asn Ser Pro Ala Ser Leu Ala Val Ser Leu Gly
1               5                   10                  15
```

```
cag agg gcc acc atc tcc tgc                                                      69
Gln Arg Ala Thr Ile Ser Cys
            20

<210> SEQ ID NO 26
<211> LENGTH: 23
<212> TYPE: PRT
<213> ORGANISM: mouse

<400> SEQUENCE: 26

Asp Ile Val Leu Thr Asn Ser Pro Ala Ser Leu Ala Val Ser Leu Gly
1               5                   10                  15

Gln Arg Ala Thr Ile Ser Cys
            20

<210> SEQ ID NO 27
<211> LENGTH: 42
<212> TYPE: DNA
<213> ORGANISM: mouse
<220> FEATURE:
<221> NAME/KEY: CDS
<222> LOCATION: (1)..(42)
<223> OTHER INFORMATION: 1F7 VL CDR1 sequence

<400> SEQUENCE: 27 aag gcc agc caa agt gtt gat tat gat ggt gat agt tat atg          42
Lys Ala Ser Gln Ser Val Asp Tyr Asp Gly Asp Ser Tyr Met
1               5                   10

<210> SEQ ID NO 28
<211> LENGTH: 14
<212> TYPE: PRT
<213> ORGANISM: mouse

<400> SEQUENCE: 28

Lys Ala Ser Gln Ser Val Asp Tyr Asp Gly Asp Ser Tyr Met
1               5                   10

<210> SEQ ID NO 29
<211> LENGTH: 45
<212> TYPE: DNA
<213> ORGANISM: mouse
<220> FEATURE:
<221> NAME/KEY: CDS
<222> LOCATION: (1)..(45)
<223> OTHER INFORMATION: 1F7 VL FR2 sequence

<400> SEQUENCE: 29 tgg tac caa cag aaa cca gga cag cca ccc aaa ctc ctc acc tat          45
Trp Tyr Gln Gln Lys Pro Gly Gln Pro Pro Lys Leu Leu Thr Tyr
1               5                   10                  15

<210> SEQ ID NO 30
<211> LENGTH: 15
<212> TYPE: PRT
<213> ORGANISM: mouse

<400> SEQUENCE: 30

Trp Tyr Gln Gln Lys Pro Gly Gln Pro Pro Lys Leu Leu Thr Tyr
1               5                   10                  15

<210> SEQ ID NO 31
<211> LENGTH: 21
<212> TYPE: DNA
<213> ORGANISM: mouse
<220> FEATURE:
<221> NAME/KEY: CDS
```

```
<222> LOCATION: (1)..(21)
<223> OTHER INFORMATION: 1F7 VL CDR2 sequence

<400> SEQUENCE: 31 gct gca tcc aat cta gaa tct                                              21
Ala Ala Ser Asn Leu Glu Ser
1               5

<210> SEQ ID NO 32
<211> LENGTH: 7
<212> TYPE: PRT
<213> ORGANISM: mouse

<400> SEQUENCE: 32

Ala Ala Ser Asn Leu Glu Ser
1               5

<210> SEQ ID NO 33
<211> LENGTH: 96
<212> TYPE: DNA
<213> ORGANISM: mouse
<220> FEATURE:
<221> NAME/KEY: CDS
<222> LOCATION: (1)..(96)
<223> OTHER INFORMATION: 1F7 VL FR3 sequence

<400> SEQUENCE: 33 ggg atc cca gcc agg ttt agt ggc agt ggg tct ggg aca gac ttc acc         48
Gly Ile Pro Ala Arg Phe Ser Gly Ser Gly Ser Gly Thr Asp Phe Thr
1               5                   10                  15 ctc aac atc cat cct gtg gag gag gag gat gct gca acc tat tac tgt         96
Leu Asn Ile His Pro Val Glu Glu Glu Asp Ala Ala Thr Tyr Tyr Cys
                20                  25                  30

<210> SEQ ID NO 34
<211> LENGTH: 32
<212> TYPE: PRT
<213> ORGANISM: mouse

<400> SEQUENCE: 34

Gly Ile Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
                20                  25                  30

<210> SEQ ID NO 35
<211> LENGTH: 27
<212> TYPE: DNA
<213> ORGANISM: mouse
<220> FEATURE:
<221> NAME/KEY: CDS
<222> LOCATION: (1)..(27)
<223> OTHER INFORMATION: 1F7 VL CDR3 sequence

<400> SEQUENCE: 35 cag ctt tgt aat gag gat cct ccc acg                                      27
Gln Leu Cys Asn Glu Asp Pro Pro Thr
1               5

<210> SEQ ID NO 36
<211> LENGTH: 9
<212> TYPE: PRT
<213> ORGANISM: mouse

<400> SEQUENCE: 36

Gln Leu Cys Asn Glu Asp Pro Pro Thr
```

-continued 1 5

<210> SEQ ID NO 37
<211> LENGTH: 30
<212> TYPE: DNA
<213> ORGANISM: mouse
<220> FEATURE:
<221> NAME/KEY: CDS
<222> LOCATION: (1)..(30)
<223> OTHER INFORMATION: 1F7 VL FR4 sequence

<400> SEQUENCE: 37 ttc ggt gct ggg acc aag ctg gag ctg aaa 30
Phe Gly Ala Gly Thr Lys Leu Glu Leu Lys
1 5 10

<210> SEQ ID NO 38
<211> LENGTH: 10
<212> TYPE: PRT
<213> ORGANISM: mouse

<400> SEQUENCE: 38

Phe Gly Ala Gly Thr Lys Leu Glu Leu Lys
1 5 10

NUCLEOTIDE SEQUENCES ENCODING VARIABLE REGIONS OF HEAVY AND LIGHT CHAINS OF MONOCLONAL ANTIBODY 1F7, AN ANTI-IDIOTYPIC ANTIBODY REACTIVE WITH ANTI-HIV ANTIBODIES

FIELD OF THE INVENTION

The present invention relates to nucleotide sequences that encode the complementarity-determining regions (CDRs) and framework regions (FR) of antibodies. The invention particularly relates to CDRs and FRs of anti-idiotypic antibodies that recognize the idiotopes of anti-HIV antibodies. The nucleotide sequences are pertinent to modulation of the immune response to HIV in HIV-1 infected individuals, as by therapeutic vaccination with the anti-idiotypic antibodies or antibody fragments they encode, as well as by direct therapeutic administration as DNA molecules.

BACKGROUND OF THE INVENTION

Acquired Immune Deficiency Syndrome (AIDS) has claimed the lives of millions of people worldwide and continues to be a leading cause of death, particularly in under-developed countries. The primary etiologic agent of AIDS is widely accepted to be one or more strains of the human immunodeficiency virus (HIV). The most studied strain of HIV is the type 1 strain (HIV-1), which is also referred to as HTLV-III. An intact HIV-1 virion is roughly spherical and presents an outer glycoprotein membrane covered with distinctive knobs and spikes.

Following initial infection with HIV is an asymptomatic stage during which the host harbors the virus and tests seropositive for HIV-1 antibodies. This stage can last as long as five years or more. This stage is followed by an AIDS-related complex stage (ARC) and, finally, AIDS. The final stage of AIDS is characterized by a variety of opportunistic infections due to the reduced vitality of the immune system. Although several drugs and drug combinations have been shown to alleviate the symptoms of AIDS and evidently reduce the viral load, to date, no effective prophylactic or therapeutic vaccine against HIV infection has been approved.

One approach proposed for the development of novel therapeutic antibodies or therapeutic vaccines, as well as prophylactic co-vaccines, employs so-called anti-idiotypic antibodies, and fragments thereof. A second strategy for modulation of immune response against viral infection involves direct inoculation of tissues in vivo with DNA encoding the VH and/or VL chains of an anti-idiotypic antibody as a therapeutic DNA vaccine.

Previously, an anti-idiotypic antibody has been shown to induce immune modulation in HIV infection. A murine anti-idiotypic antibody (designated 1F7 and produced by hybridoma ATCC Accession No. HB 11286) has been raised against pooled human anti-HIV-1 antibodies. [Mueller, S., et al., *J. Immunol.* (1991), 147:933–941]. The 1F7 idiotype is shared by human anti-HIV-1 antibodies having specificity for different proteins (envelope, core, and reverse transcriptase) of HIV-1, and the idiotype is shared by more than 70% of HIV-infected individuals. [Wang, H. et al., *Eur. J. Immunol.* (1992), 22:1749–1755]. The 1F7 idiotype occurs in high levels among patients with HIV lymphoma; however, this is shown to be due to HIV infection rather than B-cell neoplasia or abnormal B-cell proliferation. [Herndier, B., et al., *Hybridoma* (1993), 12: 529–537]. Findings suggest that the 1F7 idiotype is a marker for B-cell clones induced during the primary immune response to HIV and maintained throughout life. [Mueller, S., et al., *Hybridoma* (1997), 16: 17–21].

The potential for Mab 1F7 as a therapeutic antibody (therapeutic vaccine) has recently been demonstrated in rhesus macaques infected with a simian variant of HIV (SHIV-IIIB). [S. Mueller, et al., *PNAS* (1998) 95: 276–281; U.S. Pat. No. 6,057,421]. In these studies, a series of intravenous injections of purified 1F7 antibody enhanced and broadened the macaques' virus neutralizing antibody response to the simian virus. This result suggests the potential of beneficially modulating the immune response of chronically HIV-1 infected individuals without clinical side effects in addition to, or during breaks in, antiviral drug therapy.

The functionality of the anti-idiotypic antibody 1F7 may be exploited directly according to the following approaches:

(1) 1F7 can be applied as a post-exposure therapy to modulate the locked-in immune response and thereby facilitate an effective immune response to virus variants. Thus, a deceptive, locked-in immune response to HIV antigens is modified by applying 1F7 as therapeutic vaccine in chronically HIV-infected individuals and AIDS patients in order to achieve an immune response able to overcome virus variants that had escaped the previous, locked-in immune response set by HIV infection. (Kohler, H., et al, *Immunology Today* (1994)]. Deceptive imprinting has been described in a review as an immune reaction in HIV and parasitic infections, i.e., it is based on "Original Antigenic Sin" (OAS) of an immune response. [Veljkovic, V., et al., *Vaccine* (2001), in press]. OAS is defined for infectious pathogenic organisms such as influenza, dengue, malaria, and HIV, as imprinting or B cell dominance of the host's immune response by the antigenic make-up of the virus or parasite at first encountered during infection. The imprinting leads to an insufficient or "deceptive" immune response due to B cell dominance that prevents an adequate immune response to the challenge by a rapidly mutating virus or parasite within the host.

(2) 1F7 can be used as a prophylactic co-vaccine when applying gp120-based and other HIV protein-based prophylactic subunit vaccines in HIV seronegative individuals at risk of HIV infection. In this approach, deceptive imprinting by HIV potentially induced by subunit vaccines as recombinant gp120 (Veljkovic, et al., 2001) can be counteracted by co-administration of 1F7.

(3) 1F7 can be used during "structured therapy interruption" (STI) in HIV-infected patients treated early on with antiviral drugs. [Rosenberg, E., *Nature* (2000) 407: 523]. STI has been reported to restore a short-term immune response on T cell levels being able to fight virus variants. Co-application of the 1F7 antibody can be helpful to prolong a diversified immune response to HIV induced by STI.

In view of the demonstrated therapeutic potential of Mab 1F7 in a suitable primate model, the immunoreactive fragments of 1F7 can also be employed for therapeutic benefit. Thus, recombinant DNA techniques can be employed to isolate and manipulate the nucleotide sequences encoding the variable heavy (VH) and variable light (VL) regions of the 1F7 antibody. For instance, the variable chains of the murine antibody can be fused to the constant gamma or kappa/lambda regions of human immunoglobulins (Igs) to afford human/murine chimeras, which display the complementarity-determining regions (CDRs) and/or framework-determining regions (FRs) of 1F7. Such human/murine chimeric antibodies are expected to reduce the human anti-murine antibody (HAMA) response often encountered in passive immunization therapy, thereby affording better-tolerated vaccines. In general, such chimeric antibodies show an increase in biological half-life in vivo. They also are capable of efficiently mediating the antibody-dependent complement cascade (ADCC), antibody-dependent macrophage cytotoxicity (ADMC), and complement fixation.

Chimeric antibodies often, however, remain immunogenic in primates due to the presence of murine variable regions. Another approach to reducing the immunogenicity of murine variable regions is to mutate the VH and VL chains of the 1F7 antibody to homologous human sequences, while retaining the murine CDRs and/or FRs, i.e., the variable chains are "humanized" [Mateo, C, et al., Immunotech., (1997), 3: 71–81]. Linking the modified murine variable regions to human constant regions can afford chimeric antibodies in which the HAMA response is nullified.

The development of humanized murine antibodies has afforded exciting new therapeutics in recent years for a variety of illnesses, notably, non-Hodgkin's lymphoma, breast cancer, among others. Antibody products now account for the single largest group of biotechnology-derived molecules in clinical trials; to date, however, no antibody product has been approved for the treatment of HIV infection.

SUMMARY OF THE INVENTION

The present invention is directed to one or more isolated polynucleotides containing at least one nucleotide sequence encoding a complementarity-determining region (CDR) and/or a framework-determining region (FR) of an anti-idiotypic antibody that binds to the idiotopes of anti-HIV-1 antibodies. The aforementioned anti-idiotypic antibody is preferably Mab 1F7 produced by the hybridoma having American Type Culture Collection (ATCC) Accession No. HB 11286. Depending upon the precise nature of the polynucleotide, a single CDR, a single FR, combinations of these, or an entire variable heavy (VH) or variable light (VL) chain of the anti-idiotypic antibody can be encoded. Moreover, murine regions outside the CDRs can be mutated or replaced with human immunoglobulin sequences in order to humanize the antibody or fragment thereof.

Typically, a DNA molecule of the invention is used to obtain a polypeptide containing more than one CDR and/or FR of the 1F7 antibody. For instance, the DNA molecule can be used to transform a suitable non-human host to express a VH and/or VL chain peptide of 1F7. The VH and VL chain peptide can be fused to the corresponding constant heavy and light chain peptides for mice or humans by covalently linking the DNA molecules to the appropriate segments of the immunoglobulin genes. Whenever the complete heavy and light chains are co-expressed, an assembled murine 1F7 or human/murine chimeric analog of 1F7 is provided, which can be used in a passive immunization protocol. Alternatively, a DNA molecule encoding the at least one CDR and/or FR of the 1F7 antibody can be used directly as a DNA vaccine, e.g., by injection of muscle cells with "naked DNA". The afforded antibody product is thus: (i) a "humanized" antibody; (ii) a CDR/FR grafted antibody; or (iii) a "de-immunized" antibody with removed or altered murine antigenic residues. The therapeutic effect of such an antibody is a broadening and increase of virus neutralization.

A particularly preferred aspect of the invention employs murine nucleotide sequences encoding the CDRs of the VH and VL chains of Mab 1F7, which have the amino acid sequences shown in SEQ ID NOS: 11, 15, 19, 28, 32 and 36. Also preferred are those murine nucleotide sequences encoding the FRs of the VH and VL chains of 1F7 having the amino acid sequences shown in SEQ ID NOS: 9, 13, 17, 21, 26, 30, 34 and 38. It is to be appreciated that the present invention contemplates and includes all nucleotide sequences equivalently encoding the aforementioned murine amino acid sequences by virtue of the degeneracy of the genetic code.

DETAILED DESCRIPTION OF THE INVENTION

The present invention is directed primarily to a polynucleotide that contains one or more nucleotide sequence encoding a complementarity-determining region (CDR) and/or a framework-determining region (FR) of an anti-idiotypic antibody. Centrally of interest are anti-idiotypic antibodies that recognize (bind to) anti-HIV-1 antibodies, e.g., in sera. Particularly of interest are the CDRs and FRs of the murine monoclonal antibody 1F7 [Mueller, S., et al., J Immunol. (1991), 147:933–941].

The CDRs and FRs referred to for the present invention are those occurring in the variable heavy (VH) and variable light (VL) chains of the anti-idiotypic antibody. Typically, three CDRs and four FRs occur in the full variable chains, both heavy and light. However, it should be appreciated that the present invention is not limited to those polynucleotides encoding a complete variable chain, or even all of the CDRs or FRs of a variable chain. For instance, since a single CDR has some affinity for anti-HIV antibodies, it is of interest as a probe for the presence of these antibodies and can have a modulating effect in therapeutic regimens either alone or as part of a larger molecule.

In a preferred aspect of the invention, a polynucleotide comprises a nucleotide sequence that encodes at least one VH or VL chain CDR or FR of Mab 1F7. The amino acid sequences of the three VH CDRs, four VH FRs, three VL CDRs and four VL FRs of 1F7 are shown in the Sequence Listing according to the following assignments:

| Variable heavy chain amino acid sequences | |
|---|---|
| VH FR1: | SEQ ID NO: 9 |
| VH CDR1: | SEQ ID NO: 11 |
| VH FR2: | SEQ ID NO: 13 |
| VH CDR2: | SEQ ID NO: 15 |
| VH FR3: | SEQ ID NO: 17 |
| VH CDR3: | SEQ ID NO: 19 |
| VH FR4: | SEQ ID NO: 21 |

| Variable light chain amino acid sequences | |
|---|---|
| VL FR1: | SEQ ID NO: 26 |
| VL CDR1: | SEQ ID NO: 28 |
| VL FR2: | SEQ ID NO: 30 |
| VL CDR2: | SEQ ID NO: 32 |
| VL FR3: | SEQ ID NO: 34 |
| VL CDR3: | SEQ ID NO: 36 |
| VL FR4: | SEQ ID NO: 38 |

Generally, it is desired that a polynucleotide of the invention includes a nucleotide sequence encoding all of the CDRs and FRs of a respective VH or VL chain of 1F7 in a single molecule. An amino acid sequence of a polypeptide so expressed is shown in SEQ ID NO: 7 for a VH chain and in SEQ ID NO: 24 of a VL chain. An immune modulator polypeptide thereby expressed contains murine CDR and FR sequences. Alternatively, the polypeptide can include the respective murine CDR amino acid sequences (SEQ ID NOS: 11, 15, and 19 for VH and SEQ ID NOS: 28, 32, and 36 for VL) with these being flanked by human or primate Ig amino acid sequences, i.e., replacing the murine FRs.

A foregoing CDR and/or FR can be encoded by a native 1F7 nucleotide sequence or by a degenerate sequence that encodes the same peptide. Therefore, exemplary, but not exclusive, nucleotide sequences are those shown in the Sequence Listing according to the following assignments:

| Variable heavy chain nucleotide sequences | |
|---|---|
| VH FR1: | SEQ ID NO: 8 |
| VH CDR1: | SEQ ID NO: 10 |
| VH FR2: | SEQ ID NO: 12 |
| VH CDR2: | SEQ ID NO: 14 |
| VH FR3: | SEQ ID NO: 16 |
| VH CDR3: | SEQ ID NO: 18 |
| VH FR4: | SEQ ID NO: 20 |

| Variable light chain nucleotide sequences | |
|---|---|
| VL FR1: | SEQ ID NO: 25 |
| VL CDR1: | SEQ ID NO: 27 |
| VL FR2: | SEQ ID NO: 29 |
| VL CDR2: | SEQ ID NO: 31 |
| VL FR3: | SEQ ID NO: 33 |
| VL CDR3: | SEQ ID NO: 35 |
| VL FR4: | SEQ ID NO: 37 |

Conventionally, a polynucleotide of the invention contains a nucleotide sequence encoding all of the CDRs and FRs of a respective VH or VL chain of 1F7 in a single molecule. Exemplary nucleotide sequences, which in this case are the native sequences of 1F7, are shown in SEQ ID NOS: 5 and 22 for the full-length VH and VL genes, respectively. Alternatively, the murine nucleotide sequences encoding the CDRs, e.g., SEQ ID NOS: 10, 14, and 18 for the VH segments and SEQ ID NOS: 27, 31, and 35 for the VL segments, can be flanked by human Ig nucleotide fragments to replace the corresponding murine FRs. The human Ig sequences, e.g., constant region sequences, are operably linked in frame with the murine Ig sequences to maintain the coding integrity of the molecule and ensure correct peptide expression.

A polynucleotide of the invention can be inserted into (and conveniently stored in) a suitable vector, such as an expression plasmid, to permit transfection and expression in a suitable host cell line. The selected CDR- and/or FR-encoding nucleotide sequence is operably linked to a promoter of the vector, which promoter effects expression under conditions inherent to, or induced in, the cell line. Subsequent secretion of the resultant protein affords one or more polypeptide displaying the selected CDRs and/or FRs. Cell lines commonly employed for the expression of such immunoglobulins include myelomas, Chinese hamster ovary (CHO) cells, or insect cells.

As suggested above, a polynucleotide of the invention encoding a CDR and/or FR of 1F7 can be operably linked to a corresponding nucleotide sequence encoding a human Ig constant region to encode chimeric antibodies. For instance, a nucleotide sequence encoding the murine full-length VH chain of 1F7 can be operably linked to a nucleotide sequence encoding a human VH constant region. Likewise, the full-length VL nucleotide sequence can be operably linked to a nucleotide sequence encoding a human VL constant region. Expression of the resultant polypeptides in a suitable host can afford assembled human/murine chimeric antibodies having the desired anti-idiotypic properties, increased lifetimes, and improved tolerance.

It is anticipated that, when used as immune modulators/therapeutic vaccines, certain polypeptides generated by the polynucleotides of the present invention may stimulate a human anti-mouse antibody (HAMA) immune response in a human host due to the presence of excessive murine sequences in the molecule, which can limit therapeutic application. In such instances, it may be desired to "humanize" the sequences by incorporating appropriate human amino acid sequences in the peptide at positions flanking the murine CDRs (CDR-grafting).

Thus, in a further embodiment, a polynucleotide of the invention can be mutated using conventional recombinant DNA methods to provide homologous human Ig sequences within the VH and VL chains of 1F7 while retaining one or more of its murine CFRs and/or FRs. The CDRs of the expressed polypeptide, especially when acting in concerted fashion, can elicit or modulate an immune response to HIV infection, with the "humanized" FRs mitigating the HAMA effect, prolonging lifetimes, etc. Such humanized variable chains can additionally be linked as above to human constant regions to afford chimerics in which the murine sequences are localized to the CDRs.

Although the foregoing polynucleotides and associated polypeptides are anticipated to be particularly useful in therapeutic applications, it is anticipated that they can also be used in diagnostic applications, e.g., to detect HIV-1 infection, by virtue of their respective abilities to bind to anti-HIV antibodies in sera. Briefly, a polypeptide of the invention can be immobilized on a support and bound to a labeled ligand, e.g., an anti-HIV antibody. Loss of signal from the support in the presence of a serum sample would thereby indicate the presence of competing anti-HIV antibodies in the sample. Further protocols that can be employed, such as those employing primary and labeled secondary antibodies, as described by Self (U.S. Pat. No. 4,769,321), the disclosure of which is incorporated herein by reference. Moreover, a polypeptide of the invention can be employed in the assay protocols described by Cosand (U.S. Pat. No. 4,629,783) for synthetic peptide antigens in the detection of AIDS-related disease. Additionally, a polypeptide of the present invention can be linked to a larger non-immunogenic peptide as described by Cosand, the disclosure of which is incorporated herein by reference.

It should be appreciated that the nucleotide sequences described and claimed herein have functional equivalents by virtue of the degeneracy of the genetic code. Those equivalents are known to the skilled, or even novice, practitioner and are expressed in terms of equivalent codons for defining a given amino acid. Thus, it is contemplated that codons equivalent to those set forth in the Sequence Listing hereinafter can be substituted for those given in the Sequence Listing. Due to the vast number of equivalent nucleotide sequences afforded by the genetic code, all of the possible sequences are not set forth herein. Instead, equivalent codons are hereby identified according to the degeneracy of the genetic code as shown in Table 1 (where the U base of mRNA corresponds to the T base of DNA, cf. Stryer, L., *Biochemistry*, 1988, W. H. Freeman & Co., NY, p. 107). Thus, nucleotide sequences additional to those given in the Sequence Listing are readily identified and are contemplated within the present invention.

TABLE 1

| First Base | Second Base | | | | Third Base |
|---|---|---|---|---|---|
| | U | C | A | G | |
| U | Phe | Ser | Tyr | Cys | U |
| | Phe | Ser | Tyr | Cys | C |
| | Leu | Ser | Stop | Stop | A |
| | Leu | Ser | Stop | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

As mentioned above, it is anticipated that one aspect of the invention entails replacing those regions outside the aforementioned CDRs of the variable heavy and light chains of 1F7 with amino acid sequences from another species, e.g., human. Stated alternatively, this can involve replacing the CDRs of human antibodies with the CDRs of 1F7. This aspect of the invention is typically performed by altering a human genetic template by site-directed mutagenesis to afford the desired murine CDRs of Mab 1F7. One such method of making altered antibodies employs recombinant DNA techniques as described in U.S. Pat. No. 5,225,539, the disclosure of which is incorporated herein by reference. A further method of making humanized antibodies having one or more CDRs and possible additional amino acids, e.g., in a framework region, from a donor immunoglobulin is described in U.S. Pat. No. 5,530,101, the disclosure of which is incorporated herein by reference. A good review of recombinant CDR grafting techniques, including protocols, for providing humanized antibodies having murine CDRs is described in *Antibody Engineering*, $2^{nd}$ ed., C. Borrebaeck, ed., Chpt. 6, pp. 159–183, the disclosure of which is incorporated herein by reference. The latter reference also describes protocols for expression of humanized variable chain genes, e.g., in mammalian cells, as well as detection and purification techniques.

A further aspect of the invention concerns incorporation of an aforementioned polypeptide of the invention within a pharmaceutical composition that further contains a pharmaceutically acceptable carrier. Such carriers are well known within the art and are set forth, for example, in U.S. Pat. No. 6,057,421, which disclosure is incorporated herein by reference.

As suggested hereinabove, a polynucleotide or polypeptide of the invention can be employed to modulate the immune response of a host infected with HIV. This implementation is illustrated in U.S. Pat. No. 6,057,421, which disclosure is incorporated herein by reference. The referenced implementation concerns treatment of simian HIV-infected macaques with whole 1F7. A readily adaptable application to humans using peptide fragments of 1F7 is envisioned. Similarly, modulation of the immune response in humans infected with HIV is contemplated using one or more of an aforementioned polynucleotide, preferably a vector, encoding at least one peptide fragment of 1F7. Such a polynucleotide is conveniently administered directly to tissues, e.g., muscle tissue, of the host, either alone or in combination with a transfection-assisting agent such as a cationic lipid, liposome, or the like, as is well-known.

The present invention is further illustrated by the following example, which is offered to explain more particularly the invention, without in any way limiting it.

EXAMPLE

Determination of the VH and VL Gene Sequences of Antibody 1F7

To isolate and determine the native nucleotide sequences of the hybridoma that encodes the VH and VL genes Mab 1F7, messenger RNA was isolated from $1 \times 10^7$ cells of the HB hybridoma. First strand cDNA were synthesized using the SuperScript Preamplification System (Gibco BRL; Gaithersburg, Md.). The 1F7 heavy and light genes were amplified by PCR using the following primers:

```
1F7 heavy                             (SEQ ID NO:1)
chain:
5' primer:  5'-actagtcgacatgaaatgcagctgggtcatsttct
                                              tc-3'

(SEQ ID NO:2)
3' primer:  5'-cccaagcttacgaggggaagacatttgggaa-3'

1F7 light                             (SEQ ID NO:3)
chain:
5' primer:  5'-gggaattcatggagacagacacactcctgctat-3'

(SEQ ID NO:4)
3' primer:  5'-cccaagcttactggatggtgggaagatgga-3'
``` where s=c or g.

The amplified products were cloned in pT7 Blue T-vector (Novagen; Madison, Wis.). At least three clones were selected for sequencing with a T7 promoter primer and U-19mer primer using Sequenase Version 2.0 Kit (USB; Cleveland, Ohio).

The nucleotide sequences obtained for the VH and VL genes are shown in SEQ ID NOS: 5 and 22, respectively, and the corresponding translations are given in SEQ ID NOS: 6 and 23. The amino acid sequences of the VH and VL chains of the 1F7 antibody have been disclosed previously [Wang, Q., et al., *J. Clin. Invest.* (1995), 96: 775–780], although this reference contains errors in its FIG. 1 involving mislabeled VH and VL chains and a switching of residues 61–70 between 1F7 and M-T310 in the VL chain. Also, see U.S. Pat. No. 6,057,421. The nucleotide sequences have not been previously disclosed.

The present invention has been described with reference to particular examples and modifications thereof for purposes of clarity and understanding. It should be appreciated that further modifications and improvements are contemplated within the scope of the appended claims.

What is claimed is:

1. An isolated polynucleotide that contains a nucleotide sequence encoding at least one complementarity-determining region (COR) or framework-determining region (FR) of an anti-idiotypic antibody that binds to human or primate anti-HIV antibodies, wherein said nucleotide sequence encodes the amino acid sequence shown in SEQ ID NO: 7 or SEQ ID NO: 24.

2. The polynucleotide of claim 1, wherein said nucleotide sequence is shown in SEQ ID NO: 5 or SEQ ID NO: 22.

3. The polynucleotide of claim 1, wherein said nucleotide sequence is operably linked to a human immunoglobulin constant region nucleotide sequence.

4. A vector comprising a promoter operably linked to a nucleotide sequence encoding at least one complementarity-determining region (CDR) or framework-determining region (FR) of monoclonal antibody 1F7, wherein said nucleotide sequence encodes the amino acid sequence shown in SEQ ID NO: 7 or SEQ ID NO: 24.

5. The vector of claim 4, wherein said nucleotide sequence is operably linked to a human immunoglobulin constant region nucleotide sequence.

6. The vector of claim 4 wherein said nucleotide sequence is shown in SEQ ID NO: 5 or SEQ ID NO: 22.

7. A cell line transformed with the vector of claim 4.

8. A method of modulating the immune response of a host infected with HIV comprising administering the polynucleotide of claim 1 to tissues of the host.

9. A method of modulating the immune response of a host infected with HIV comprising administering the vector of claim 4 to the host.

* * * * *